(12) United States Patent
El-Bialy et al.

(10) Patent No.: US 8,079,966 B2
(45) Date of Patent: Dec. 20, 2011

(54) ULTRASOUND STIMULATION DEVICES AND TECHNIQUES

(75) Inventors: Tarek Hessin Ahmed El-Bialy, Edmonton (CA); Jie Chen, Edmonton (CA); Ying Yin Tsui, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 1023 days.

(21) Appl. No.: 11/798,123

(22) Filed: May 10, 2007

(65) Prior Publication Data

US 2008/0021327 A1 Jan. 24, 2008

Related U.S. Application Data

(60) Provisional application No. 60/799,644, filed on May 12, 2006.

(51) Int. Cl.
*A61N 7/00* (2006.01)
*A61B 8/00* (2006.01)

(52) U.S. Cl. ................. 601/2; 600/459; 607/51
(58) Field of Classification Search ............ None
See application file for complete search history.

(56) References Cited

U.S. PATENT DOCUMENTS

| | | | | |
|---|---|---|---|---|
| 5,496,256 A | * | 3/1996 | Bock et al. | 601/2 |
| 2002/0103435 A1 | * | 8/2002 | Mault | 600/439 |
| 2003/0225331 A1 | * | 12/2003 | Diederich et al. | 600/437 |
| 2004/0015106 A1 | | 1/2004 | Coleman | |
| 2005/0070797 A1 | * | 3/2005 | Cadossi et al. | 600/438 |
| 2005/0249667 A1 | | 11/2005 | Tusznski et al. | |
| 2006/0051328 A1 | | 3/2006 | Johnson | |
| 2006/0241530 A1 | | 10/2006 | Ostrovsky et al. | |
| 2007/0065420 A1 | * | 3/2007 | Johnson | 424/93.7 |

OTHER PUBLICATIONS

Yingda Chen, Jie Chen and Tie Lv, "A High Order Bi-phase Modulation Scheme for UWB Transmission". International Conference on Vehicular Technology 2004, Los Angeles, Sep. 2004.*
L. Andersson, "Dentoalveolar ankylosis and associated root resorption in replanted teeth. Experimental and clinical studies in monkeys and man". Swed Dent J Suppl, 1998;56: 175.
M. Trope, "Luxation injuries and external root resorption etiology, treatment and prognosis". J Calif Dent Assoc, 2000;28: 860-6.
E. J. Barret and D. J. Kenny. "Avulsed permanent teeth: a review of the literature and treatment guidelines". Endod Dent Traumatol, 1997;13: 153-63.
S. Baumrind, E. Korn, and R. Boyd, "Apical root resorption in orthodontically treated adults". AJODO, 1996;110:311-20.
J. Mah, et. al, "Current status of root resorption". Biological Mechanics of Tooth Movement and Craniofacial Adaptation, Harvard Society for the Advancement of Orthodontics, 2000; 195-200.

(Continued)

*Primary Examiner* — Long V. Le
*Assistant Examiner* — Farshad Negarestan
(74) *Attorney, Agent, or Firm* — Marsh Fischmann & Breyfogle LLP

(57) ABSTRACT

Ultrasound stimulation devices and related techniques are disclosed. An ultrasound transducer for generating ultrasound energy is carried by a transducer housing that seals the transducer and may also include a positioning element for positioning the transducer proximate an application area to which generated ultrasound energy is to be applied. The transducer housing may also carry such components as a battery, a wireless receiver, and a controller. The same housing or a separate sensor housing may include an ultrasound sensor that provides feedback to the ultrasound transducer or its controller, illustratively through a wireless transmitter.

9 Claims, 11 Drawing Sheets

OTHER PUBLICATIONS

B. E. Machen, "Legal aspects of orthodontic practice: risk management concepts. Diagnosis, root resorption, and progress monitoring". AJODO, 1989;95:267-8.

M. K. Caliskan and M. Turkun, "Prognosis of permanent teeth with internal resorption: a clinical review". Endod Dent Traumatol, 1997;13: 75-81.

J. P. Schatz, C. Hausherr, J. P. Joho, "A retrospective clinical and radiologic study of teeth reimplanted following traumatic avulsion". Endod Dent Traumatol, 1995;11: 235-9.

M. Trope, "Root resorption of dental and traumatic origin: classification based on etiology". Pract Periodontics Aesthet Dent, 1999;10: 515-22.

A. Majorana, E. Bardellini, G. Conti, E. Keller, S. Pasini, "Root resorption in dental trauma: 45 cases followed for 5 years". Dental Traumatology, 19 (5): 262-265, 2003.

Iiker Alat, et. al., "The mechanical or electrical induction of medullary angiogenesis: will it improve sternal wound healing?". Medullary angiogenesis for sternal wound healing; vol. 31, No. 4, 2004, pp. 363-367.

C. Saltzman, A. Lightfoot, and A. Amendola, "PEMF as Treatment for Delayed Healing of Foot and Ankle Arthrodesis". Foot & Ankle International; vol. 25, No. 11 pp. 771-773, 2004.

T. H. El-Bialy, T. J. Royston, R. L. Magin, C. A. Evans, A. M. Zaki, and L. A. Frizzell, "The effect of pulsed ultrasound on mandibular distraction". Ann. Biomed. Eng., 2002;30(10):1251-61.

T. H. El-Bilay, A. E. Zaki and C. A. Evans "Effect of ultrasound on rabbit mandibular incisor formation and eruption after mandibular osteodistraction". AJODO, 2003;124:427-34.

T. El-Bialy, I. El-Shamy, T. M. Graber, "Repair of orthodontically induced root resorption by ultra-sound in humans". Am. J. Orthod. Dentofac. Orthop. 126(2): 186-93, Aug. 2004.

T. El-Bialy, et. al., "Treatment of Hemifacial Microsomia without Surgery: An Evidence-Based Approach". Proceeding of 6th International Congress, World Federation of Orthodontists, Sep. 8, 2005.

Jie Chen, Tiejun Lv, Yingda Chen, and Jingyang Lv, "A Timing-jitter Robust UWB Modulation Scheme". IEEE Signal Processing Letters, vol. 13, No. 10, pp. 593-596, Oct. 2006.

W.T. Ang, Jie Chen, and Tiejun Lv, "High-order Monocycle Design and Its Waveform-Generation Circuit for UWB Communications". IEEE Trans. on Circuits and Systems, vol. 4, No. 8, pp. 1657-1665, Aug. 2007.

Yingda Chen, Jie Chen and Tie Lv, "A High Order Bi-phase Modulation Scheme for UWB Transmission". International Conference on Vehicular Technology 2004, Los Angeles, Sep. 2004, pp. 5209-5213.

A. Hajimiri and T. H. Lee, "A General Theory of Phase Noise in Electrical Oscillators". IEEE Journal of Solid-state Circuits, vol. 33, No. 2, pp. 179-194, Feb. 1998.

N. Retdian, S. Takagi, and N. Fujii, "Voltage Controlled Ring Oscillator with Wide Tuning Range and Fast Voltage Swing". IEEE Asia-Pacific Conference on ASIC, 2002, pp. 201-204.

C. L. Tsai, W. H. Chang, and T. K. Liu, "Preliminary studies of duration and intensity of ultrasonic treatments on fracture Repair". Chin. J. Physiol. 35:21-26, 1992.

D. A. Dalla-Bona, E. Tanaka, H. Oka, E. Yamano, N. Kawai, M. Miyauchi, T. Takata, K. Tanne, "Effects of ultrasound on cementoblast metabolism in vitro". Ultrasound Med Biol., Jun. 2006;32(6):943-8.

International Search Report established for PCT Application Serial No. PCT/CA2007/000822, completed Jul. 24, 2007, mailed Aug. 21, 2007.

* cited by examiner

ULTRASOUND STIMULATION DEVICES AND TECHNIQUES

CROSS-REFERENCE TO RELATED APPLICATION

The present patent application claims the benefit of U.S. Provisional Patent Application Ser. No. 60/799,644, entitled "ULTRASOUND STIMULATION DEVICES", and filed on May 12, 2006, the entire contents of which are incorporated herein by reference.

FIELD OF THE INVENTION

This invention relates generally to ultrasound stimulation and, in particular, to devices and techniques for applying ultrasound stimulation.

BACKGROUND

Biological tissue/bone healing and growth have recently attracted a great deal of research interest in various medical fields. For example, after traumatic luxation and avulsion injury to teeth, root resorption becomes a major concern [1, 2, 3]. A favorable crown to root ratio is important to support a tooth and to withstand occlusal forces. Increased root resorption is commonly observed during orthodontic tooth movement in humans [4].

In severe resorption, where the teeth crown to root ratio is adversely affected, increased teeth mobility is often observed in patients and splinting of these teeth may be required in some patients [5]. Another adverse outcome of teeth root resorption is the increased liability facing orthodontists from malpractice claims [6]. The healing pattern generally depends on the degree and surface area of the damaged root and on the nature of an inflammatory stimulus [2, 7]. If the root damage is small, it can be healed by new cementum. However, if the root damage is large, bone may attach directly onto the root surface resulting in ankylosis; thereafter osseous replacement and healing by new cementum is questionable [8, 9]. Infection can cause progressive inflammatory resorption that can in turn cause tooth loss in a very short period of time.

It has been reported that 66% of tooth loss following trauma is due to root resorption and half of these cases involve a progressive type of root resorption [10]. Non-invasive methods for tissue healing include electric stimulation [11], pulsed electromagnetic field (PEMF) [12], and low intensity pulsed ultrasound (LIPUS) [13]. In animal studies involving rabbits, a LIPUS device has been used for bone healing and formation during mandibular distraction osteogenesis [13]. LIPUS has also been used to stimulate dental tissue formation and enhance teeth eruption [14]. In human studies, a LIPUS device has been used for the healing of orthodontically-induced teeth root resorption [15] and this was supported by other in-vitro studies [23].

Studies show that with suitable pulse durations and power densities, LIPUS pulses are very effective for enhancing dental-tissue healing and for treating the tooth-shortening problem. A congenital anomaly known as Hemifacial microsomia, characterized by an underdeveloped mandible (lower jaw) on one side, has also been treated using a LIPUS device to stimulate bone growth in the deficient side, giving patients a more symmetric jawline [16].

Although success in using therapeutic ultrasound has been repeatedly demonstrated, devices that are traditionally used for applying ultrasound to a treatment area are bulky, and require a patient to hold the device in place during treatment. Control of the intensity of ultrasound applied by these devices also tends to be difficult. For example, currently available devices use wired communications, and the possibility of saliva contacting a wire may cause short circuits and endanger a patient.

SUMMARY OF THE INVENTION

Thus, there remains a need for improved devices and techniques for applying ultrasound stimulation.

According to an aspect of the invention, a device includes an ultrasound transducer operable to generate ultrasound energy, a transducer housing for carrying the ultrasound transducer, and a transducer positioning element operable to position the ultrasound transducer proximate an application area to which the generated ultrasound energy is to be applied.

The transducer housing may include a transducer portion for carrying the ultrasound transducer, and a positioning portion comprising the transducer positioning element.

The transducer positioning element may be operable to releasably mount the transducer housing to a support. The support may be a tooth or other intra-oral structure, for example.

In some embodiments, the ultrasound transducer comprises a low intensity pulsed ultrasound (LIPUS) transducer.

The device may also include a battery disposed in the transducer housing and operatively coupled to the ultrasound transducer.

The transducer positioning element may include, for example, one of: an element for attachment to an orthodontic bracket that is fastened to the tooth or other intra-oral structure, and an element for attachment to the tooth or other intra-oral structure.

A controller is disposed in the transducer housing in some embodiments and is operatively coupled to the ultrasound transducer. The controller is operable to control an intensity of the ultrasound energy generated by the ultrasound transducer.

The device may also include an ultrasound sensor operable to sense the ultrasound energy generated by the ultrasound transducer, and to provide a feedback signal to the controller.

A wireless transmitter may be operatively coupled to the ultrasound sensor, and a wireless receiver disposed in the transducer housing may be operatively coupled to the controller, in which case the feedback signal is transmitted from the ultrasound sensor through the wireless transmitter and is received by the controller through the wireless receiver. The wireless transmitter and the wireless receiver may be an ultra-wideband (UWB) transmitter and a UWB receiver, respectively.

In some embodiments, the device includes a sensor housing for carrying the ultrasound sensor, and a sensor positioning element operable to position the sensor proximate a sensing area at which ultrasound energy is to be sensed. The transducer positioning element may comprise the sensor positioning element.

The transducer positioning element and the sensor positioning element include, in some embodiments, a combination selected from a group consisting of: the transducer positioning element comprising an element for attachment to an orthodontic bracket that is fastened to a tooth or other intra-oral structure, and the sensor positioning element comprising a plate structured for retention by a portion of an oral cavity, the transducer positioning element and the sensor positioning element comprising a tooth crown for attachment to the tooth, the transducer positioning element and the sensor positioning element comprising respective elements for releasably retaining the transducer housing and the sensor housing at respective portions of a body of a patient proximate the application area and the sensing area, the transducer positioning element and the sensor positioning element comprising an element for releasably retaining both the transducer housing and the sensor housing at one or more portions of a body of a patient proximate the application area and the sensing area, and the transducer positioning element and the sensor positioning element comprising respective elements for positioning the transducer and the sensor relative to a cell culture.

Such a device may be used, for example, for provision of ultrasound stimulation to stem cells.

A method of making an ultrasound stimulation device is also provided, and includes providing a transducer housing for carrying an ultrasound transducer, providing a transducer positioning element operable to position the ultrasound transducer proximate an application area to which ultrasound energy is to be applied, and installing in the transducer housing an ultrasound transducer operable to generate ultrasound energy.

The operation of providing a transducer positioning element may involve forming the transducer positioning element as part of the transducer housing.

Providing a transducer housing may also or instead involve moulding the transducer housing.

The method may also include installing a battery in the transducer housing, and connecting the battery to the ultrasound transducer.

In some embodiments, the method includes installing a controller in the transducer housing, and connecting the controller to the ultrasound transducer, the controller being operable to control an intensity of the ultrasound energy generated by the ultrasound transducer.

The method may further include installing a wireless receiver in the transducer housing, and connecting the wireless receiver to the controller, the wireless receiver being operable to receive a feedback signal from an ultrasound sensor and to provide the received feedback signal to the controller.

In some embodiments, the method includes providing a sensor housing, and installing in the sensor housing the ultrasound sensor and a wireless transmitter operatively coupled to the ultrasound sensor.

A device according to another aspect of the invention includes an ultrasound sensor operable to sense an intensity of ultrasound energy at a sensing area, the ultrasound energy being generated by an ultrasound transducer that is controlled by a controller based on a feedback signal from the ultrasound sensor, a wireless transmitter operatively coupled to the ultrasound sensor and operable to transmit the feedback signal from the ultrasound sensor to the controller, a sensor housing for carrying the ultrasound sensor, and a sensor positioning element operable to position the ultrasound sensor proximate the sensing area.

The wireless transmitter may be a UWB transmitter, for example.

A self-contained ultrasound stimulation device is also provided, and includes an ultrasound transducer unit comprising an ultrasound transducer operable to generate ultrasound energy, a controller operatively coupled to the ultrasound transducer and operable to control the ultrasound transducer based on a feedback signal, and a wireless receiver operatively coupled to the controller, a transducer housing sealing the ultrasound transducer unit, an ultrasound sensor unit comprising an ultrasound sensor operable to sense ultrasound energy at a sensing area and to generate the feedback signal based on sensed ultrasound energy, and a wireless transmitter operatively coupled to the ultrasound sensor and operable to transmit the feedback signal to the ultrasound transducer unit, and a sensor housing sealing the ultrasound transducer.

This type of device may be used, for instance, for stimulation of stem cells in a cell culture located between the ultrasound transducer unit and the ultrasound sensor unit. In one embodiment, such a device is used for stimulation of stem cells in a cell culture in which one of the ultrasound transducer unit and the ultrasound sensor unit is floated.

Other aspects and features of embodiments of the present invention will become apparent to those ordinarily skilled in the art upon review of the following description.

BRIEF DESCRIPTION OF THE DRAWINGS

Examples of embodiments of the invention will now be described in greater detail with reference to the accompanying drawings.

DETAILED DESCRIPTION OF PREFERRED EMBODIMENTS

Figure 1:
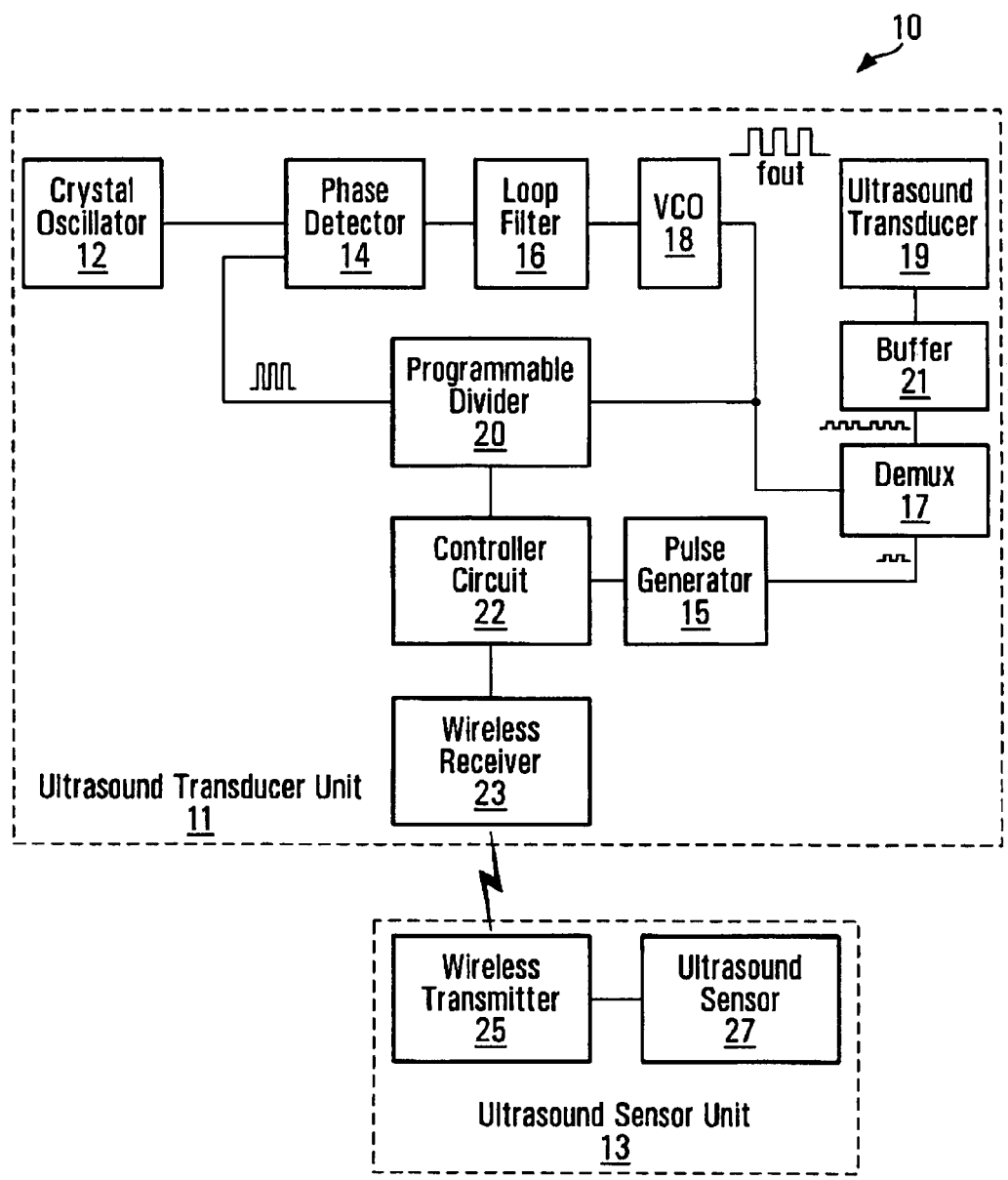
FIG. 1 is a block diagram of a device according to an embodiment of the invention.

In some embodiments of the invention, a LIPUS device is miniaturized for intra-oral usage. Specifically, designs according to such embodiments of the invention may include any or all of the following aspects:

1) reducing the size of the ultrasound transducer so that it can be used comfortably inside a patient's mouth;
2) miniaturized LIPUS devices using wireless connections so that saliva from patients' mouths will not cause short circuits and thus endanger the patients;
3) the device and a battery may be packed in biocompatible materials, such that the resulting devices may be mountable onto an orthodontic bracket, or even directly to a tooth using a plastic tooth crown (removable crowns, only for LIPUS application), for example, to avoid the need for patients to press down on or otherwise hold a transducer in place to ensure tight contact with gingival tissues;

4) an energy sensor is utilized to evaluate the degree of power impedance and the effective LIPUS power that reaches teeth roots within the bone, and may be housed behind the palatal bone in an acrylic plate, for instance.

A system-on-a-chip (SoC) solution is one possible implementation of a miniaturized wireless-controlled LIPUS device, which could be used to non-invasively and safely enhance dental tissue healing and/or to stimulate bone growth, or more generally to provide targeted ultrasonic stimulation.

A miniaturized LIPUS transducer that has a size of about a square centimetre could be housed in an intra-oral device that fits comfortably inside a patient's mouth, although other sizes of transducers and/or different types of transducers may also be suitable for this purpose. An intra-oral wireless device can be utilized, for example, to prevent tooth root material loss and/or to enhance dental tissue healing/bone growth or bone supporting teeth loss thus preventing tooth loss.

In some embodiments, an intra-oral device is "smart", in the sense that intelligent control may be provided by implementing a feedback control loop. A wireless feedback control loop might be provided using ultra-wideband (UWB) wireless communication techniques. UWB is a relatively new short-range communication system.

UWB's carrier-less nature provide the advantages of better penetration and low-power transmission compared to the penetration and transmission power of conventional wireless systems. Since UWB signals spread from 0 to a few GHz at a very low signal level, they do not cause interference to ultrasound transducers. UWB, moreover, is complementary to ultrasound tissue stimulation.

As noted above, device miniaturization may come from an embedded SoC design, by using microfabrication technology. The resulting product(s) can be tailored to varying sizes of teeth or biological tissue which are in need of ultrasound stimulation. Devices according to some embodiments of the invention as disclosed herein are non-invasive and may be sold, for example, for intra-oral use.

The operating circuit of an ultrasound stimulation may produce a desired pulse waveform, such as a waveform with a modulation characteristic of "ON" for 200 μs and "OFF" for 800 μs, and output power densities up to 30 mW/cm$^2$. The outputs of such a device may match existing LIPUS outputs that produced the significant biological effects mentioned above.

FIG. 1 is a block diagram of a device according to an embodiment of the invention. It should be appreciated that FIG. 1 represents only one embodiment of the invention, and that other embodiments may include further, fewer, or different components interconnected in a similar or different manner than explicitly shown. For example, although a battery or other power source might be provided for an ultrasound transducer unit and an ultrasound sensor unit, power sources have not been explicitly shown in FIG. 1 so as to avoid overly complicating the drawing. The contents of the other drawings are similarly illustrative and do not limit the scope of the present invention.

The device 10 includes an ultrasound transducer unit 11 and an ultrasound sensor unit 13, although both units need not be provided in all embodiments. The ultrasound transducer unit 11 may include any of various forms of an ultrasound transducer 19 that is operable to generate ultrasound energy and components for driving the transducer. In the device 10, the ultrasound transducer unit 11 includes a crystal oscillator 12 operatively coupled to a phase detector 14, which is operatively coupled to a programmable divider 20. The phase detector 14 is also operatively coupled to a loop filter 16, which in turn is operatively coupled to a VCO 18. The VCO 18 is operatively coupled to the programmable divider 20 and to a demultiplexer (DEMUX) 17. A controller circuit 22 is operatively coupled to the programmable divider 20 and to a pulse generator 15, which is operatively coupled to the DEMUX 17. The DEMUX 17 provides a drive signal to the ultrasound transducer 19 through a buffer 21 in the example shown. The drive signal is based on outputs of the VCO 18 and the pulse generator 15. The controller circuit 22 is also operatively coupled to a wireless receiver 23 in the example shown in FIG. 1.

The amplitude and frequency, $f_{out}$, of the VCO 18 output, and thus the drive signal provided to the ultrasound transducer 19, may be in the range of 40 kHz and above, for example, and can be tuned by the controller circuit 22. The controller circuit 22, also referred to more generally herein as a controller, may receive feedback from an ultrasound sensor 27 of the ultrasound sensor unit 13 through a wireless transmitter 25 and the wireless receiver 23, for instance, and cause the amplitude and frequency of the VCO 18 output and thus the drive signal to vary accordingly. The drive signal is used as the input of the ultrasonic transducer 19.

In one design, a CMOS Phase Locked Loop (PLL) is used to implement the phase detector 14, the loop filter 16, the VCO 18, and the programmable divider 20 shown in FIG. 1. Implementations using other types of devices are also contemplated. Those skilled in the art will be familiar with PLLs and other possible implementations of the components shown in FIG. 1 and their operation.

Figure 2A:
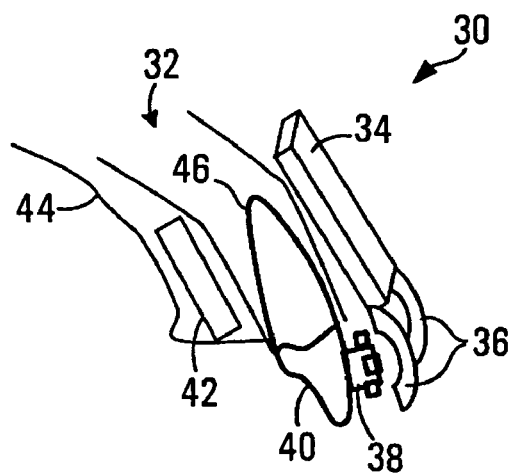
FIGS. 2A and 2B are side and plan views, respectively, illustrating the use of an intra-oral device of an embodiment of the invention.
Figure 2B:
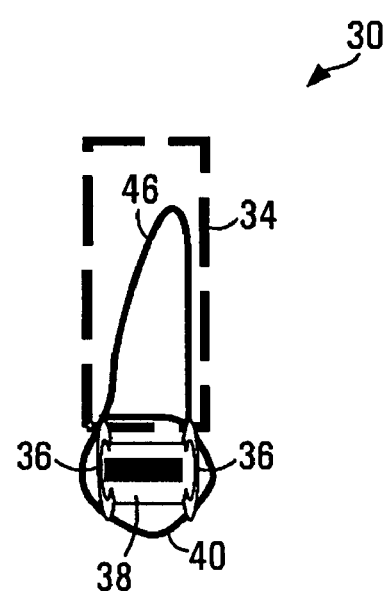

FIGS. 2A and 2B are side and plan views illustrating the use of an intra-oral device of an embodiment of the invention. The example device 30 includes a transducer housing 34, which can be provided in any of various sizes, and a positioning element 36 that can be mounted onto an intra-oral structure such as an individual tooth 40, as shown, to position an ultrasound transducer carried by the transducer housing 34 proximate an application area to which ultrasound energy is to be applied. The transducer housing 34 carries a miniaturized ultrasound transducer, such as a LIPUS transducer. In the example shown, the ultrasound transducer is carried inside the transducer housing 34.

Figure 3:
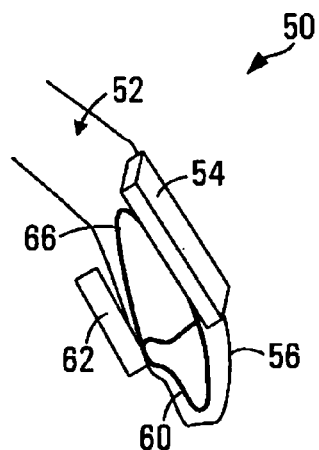
FIG. 3 is a side view illustrating the use of an intra-oral device of another embodiment of the invention.

The device 30 shown in FIGS. 2A and 2B is designed with a positioning element 36 in the form of clips or hooks, illustratively stainless steel clips or hooks, to be attached to an orthodontic bracket 38. This type of positioning element 36 thereby "indirectly" mounts the transducer housing 34 to a tooth 40. Another possible embodiment of a transducer housing and a transducer positioning element is a tooth crown, such as a plastic crown. The tooth crown could be removable and only used for LIPUS application. One such device is shown in FIG. 3 and described below.

The relative locations of the positioning element 36 and the transducer housing 34 are such that the ultrasound transducer carried by the transducer housing is positioned adjacent or proximate to an application area to which ultrasound energy is to be applied when the transducer housing is mounted on a tooth. Those skilled in the art will appreciate that although it may generally be desirable to have the transducer housing 34 in contact with an application area, some degree of separation between an ultrasound transducer and an application area may be acceptable.

In the example shown in FIGS. 2A and 2B, the application area is generally the root 46 above the tooth 40 on which the device 30 is to be mounted, although offset positions are also possible, such as to allow the device to be mounted to one tooth for application of ultrasound energy to a different tooth or portion of a jaw 32.

A shelf, cavity, or any of various other structures may be used in or on the transducer housing to carry a transducer and/or possibly associated components such as a battery, a controller, and a wireless receiver.

The device 30 shown in FIG. 2A also includes a sensor 42 carried by a different housing 44, which may be an acrylic plate fabricated from self-curing acrylic resin, for example. Such a plate can be easily fabricated from a patient's dental cast, which is a positive replica of a portion of the patient's oral cavity, specifically the teeth and jaw, so that the plate can be worn by a patient and retained inside the mouth. Orthodontic stainless steel clasps or hooks, a friction fit, or some other arrangement might then be used to retain the plate in place.

In other embodiments, both a transducer and a sensor are positioned using the same positioning element. Transducer and sensor housings could be located relative to the positioning element so that the transducer and sensor are positioned proximate application and sensing areas, generally overlapping each other as shown in FIG. 2A, for example, when the housings are mounted on a tooth or other support.

FIG. 3 is a side view illustrating the use of an intra-oral device of another embodiment of the invention, wherein the same positioning element is used for a transducer and a sensor. As shown, the device 50 includes a transducer housing 54 carrying an ultrasound transducer, a sensor housing 62 carrying a sensor, and a positioning element 56 in the form of a removable crown for mounting the device 50 to a tooth 60. The device 50 may be used to provide ultrasound stimulation to the root 66 of the tooth 60, and/or to a different tooth, root or portion of a jaw 52.

The transducer housing 54 and/or the sensor housing 62 may be in the form of an acrylic plate that is bonded or otherwise attached to the crown 56, which may be an acrylic or polycarbonate crown for instance. The housings 54, 62 and the crown 56 could instead be integrated into a single housing that includes a transducer portion for carrying the transducer, a sensor portion for carrying the sensor, and a positioning portion for positioning the transducer and the sensor.

The housing(s) for an intra-oral device could be fabricated in any of various ways. Any or all of a positioning element, a transducer housing, and a sensor housing could be milled or otherwise formed in a housing "blank". Moulding or casting represent examples of other fabrication processes. In another possible process, identical copies of the devices are mass produced and then for each device, its housing(s) can be customized to the desired shape and size to fit an individual patient using techniques such as laser machining.

It should also be appreciated that the present invention is in no way restricted to a one-piece housing. The bracket clips 36 shown in FIGS. 2A and 2B, for example could be provided as separate components and attached to a transducer housing during device manufacture, or possibly later to provide for adjustment of the relative positions of the clip and the transducer for different mounting and application area geometries. The plate 44 could also be formed around the sensor 42 after a cast of a patient's teeth and jaw is taken. Similarly, the crown 56 could be provided separately from the transducer housing 54 and/or the sensor housing 62, with those housings later being bonded or otherwise attached to the crown.

Mechanisms for allowing adjustment of the relative positions of a transducer and/or sensor are also possible, to ensure that a transducer is properly located proximate and possibly in contact with an application area and that a sensor is properly located to sense energy from the transducer, for example.

Designs as shown in FIGS. 2A and 2B and in FIG. 3 eliminate the need for a patient to bite down on or otherwise hold a device for a treatment period, which may be 20 minutes per day in some cases. In one embodiment, the device parts are housed in acrylic plates of 0.5 mm thickness, although other biocompatible materials might instead be used to seal parts of the device. These types of housings serve as electrical insulators to reduce the risk of a patient experiencing a short circuit between device components and any filling material within the patient's mouth, for example, or through other liquids or material in different applications.

In some embodiments, the dimensions of the transducer are 5-10 mm wide, depending on the size of the patient's tooth or teeth and the size of the application area, and 10-15 mm long with 1 mm thickness to fit different tooth-root lengths, for example. The acrylic cover material, which itself may form the housing(s), may also be hard enough to withstand pressure and handling (2-3 psi).

The transducer material may be a thin poly vinylidene fluoride (PVDF) that is commercially available and can be cut to any suitable dimensions and packed with a miniaturized driving and control circuit and one or more batteries, illustratively button batteries. This assembly may be covered with an acrylic housing and, for example, either mounted to orthodontic brackets using stainless steel hooks or bonded to acrylic or plastic temporary teeth crowns to hold the transducer in place during the LIPUS application. The acrylic or plastic crowns could be very thin (about 0.5-0.25 mm thickness) and thus well tolerated by patients without any problem or major adjustments. If adjustments are needed, they can be easily made at the dentist/orthodontist office when the miniaturized device is first prescribed.

For wireless sensor feedback, a high-order monocycle (HOM) UWB modulation scheme may be used to overcome time-jitter problems. Simulation results demonstrate that HOM is more robust than the conventional UWB design using the Rayleigh waveform. Several designs have been presented in transactions and conference proceedings [17, 18, 19]. HOM designs, and possibly other schemes, can be used to operatively couple a sensor with a transducer. A UWB transmitter and receiver can provide an appropriate feedback channel for controlling the emitted ultrasound power level in order to ensure that the ultrasound device operates within an optimum level. A closed loop design may be provided, for example, using two chips, including one for the transducer and the other for energy sensing.

Major orthodontic and endodontic materials supply companies are actively looking for solutions to enhance dental-tissue and bone growth stimulation and healing. Devices according to embodiments of the invention can potentially provide safe and low-cost treatment for tooth-root fracture and tooth-root resorption, and can be easily adapted for industrial use. In addition to many applications for dental care, the device can also be modified for other tissue growth stimulation healing. For example, in Hemifacial Microsomia, or underdeveloped mandible, a device as disclosed herein can be used to stimulate bone growth in the deficient side, giving patients a more symmetric jawline.

Embodiments of the invention have been described above primarily in the context of physical structures and features. However, internal design aspects of intra-oral ultrasound devices have also been considered.

Currently, several prospective implementation techniques exist. For example, one can use an inductance-capacitance VCO or a ring oscillator. An advantage of the first design is that the resulting circuit has low phase noise, but it also has limited tunable frequency range and is difficult to implement in silicon. The ring oscillator design has a wider tuning range and is easy to implement. For a 40 kHz and higher tuning range, a ring oscillator approach may be preferred.

Figure 4:
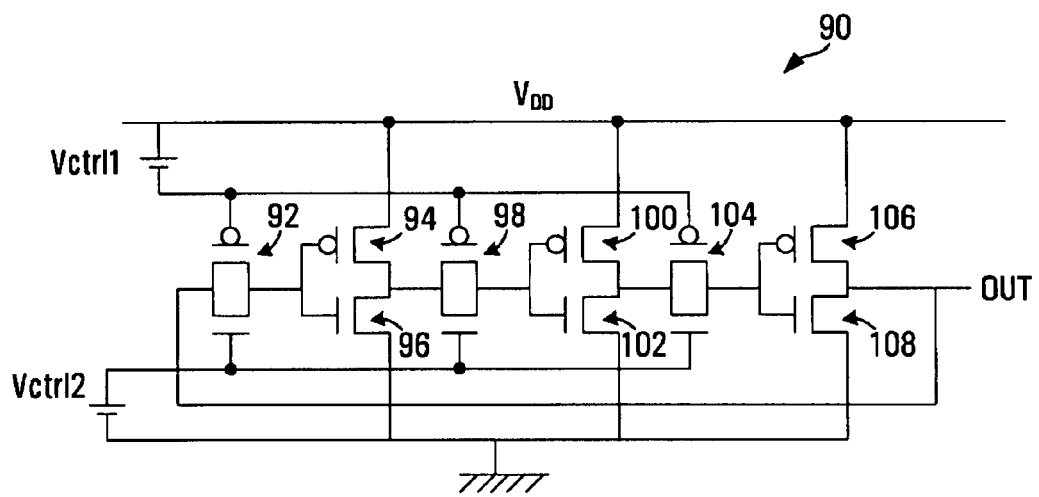
FIG. 4 is a schematic diagram of a Complementary Metal Oxide Semiconductor (CMOS) oscillator.

An example ring oscillator design is shown in FIG. 4. The CMOS ring oscillator 90 includes transmission gates 92, 98, 104, which are interconnected to provide positive feedback in order to satisfy Barkhausen's criteria (gain>1, phase difference=360°). In this CMOS oscillator 90, transistors 94, 96, 100, 102, 106, 108 are operatively coupled between $V_{DD}$ and ground potential, and transmission gates 92, 98, 104 are operatively coupled between $V_{DD}$-$V_{ctrl1}$ and $V_{ctrl2}$. The oscillation frequencies are varied by $V_{ctrl1}$ and $V_{ctrl2}$, which control the effective resistance of the transmission gates 92, 98, 104.

UWB signals and LIPUS are complementary in some embodiments, with UWB being for wireless control, and LIPUS being for ultrasound stimulation. A LIPUS device may work at 1.5 MHz while UWB can spread from 0 to GHz frequency, for instance. Ultrasound stimulation can potentially be applied to various application areas simultaneously by networking multiple transducers and their associated UWB transmitters together. A time-hopping binary symbol emitted by the UWB transmitter at the $k^{th}$ tooth, $s_{tr}^{(k)}(u,t)$, in time-hopping high-order modulation (HOM) can be written as $$s_{tr}^{(k)}(u,t) = \sum_{j=0}^{N_s-1} (1 - 2D^{(k)}(u)) \cdot \omega_{tr}(t - jT_f - c_j^{(k)}(u)T_c),$$

where
$D^{(k)}(u) \in \{0,1\}$ is a transmitted symbol bit from the $k^{th}$ tooth's UWB transmitter;
$N_s$ impulses are employed per symbol bit in time-hopping UWB modulation;
t is the transmitter's clock time;
$\omega_{tr}(\ldots)$ represents a transmitted impulse waveform function or a monocycle;
u indicates a point in an underlying probability sample space;
$c_j^{(k)}(u)$ is a pseudo-random time-hopping pattern of the $k^{th}$ transmitter introduced to avoid symbols from various UWB transmitters colliding with each other in a multi-access environment;
$T_c$ is chip duration.

A device as shown in FIGS. 2A and 2B and in FIG. 3 may include an ultrasound generator and a UWB receiver in a transducer housing 34, 54, and an ultrasound energy detector and a UWB transmitter in a sensor housing 44, 62. One example of an ultrasound generator has been discussed previously. With respect to UWB transmitter design, one embodiment uses a microcontroller coupled with a fast digital to analog converter (DAC) to generate desired UWB monocycles. The UWB waveforms could be stored in memory and read out when needed. The output power at the ultrasound transducer can be adjusted automatically based on the energy sensor's power measurement to achieve optimum output power intensity, illustratively 30 mW/cm² at the transducer's surface. The value of 30 mW/cm² is based on previous research that examined the effects of pulsed ultrasound on animal models at different power intensities [22]. The available output power is limited to a maximum value in some embodiments in order to prevent overheating dental or other tissues.

With respect to the UWB receiver design, the receiver may decode a received symbol based on decision statistics, $\theta_j = \int r(u,t-t_j)v(t)dt$, assuming perfect knowledge about the channel. In this decision statistics expression, $t_j$ represents asynchronization caused by timing-jitter and other channel impairments, and $\theta_j$ is the correlation between the received signals $$r(u,t) = \sum_{k=1}^{N_u} A_k s_{rec}^{(k)}(t - \tau^{(k)}(u)) + n(u,t)$$

and template waveforms $$v(t) = \omega_{rec}(t - jT_f - c_j^{(t)}T_c - \tau^{(t)}),$$

where
$T_f$ is a time-window in which each individual pulse can move around;
$T_c$ is the pulse position with reference to the boundary of $T_f$;
$A_k$ is the gain of the $k^{th}$ transmitter;
$\tau^{(k)}(u)$ is a random variable representing the time asynchronism; and
$n(u,t)$ represents Gaussian thermal noise.

The energy detector can be designed, for example, to measure only the power spectrum density for the signal in the frequency range above 40 kHz. The transducer and the energy sensor work together. If the transducer does not generate ultrasound, the energy sensor may inform the patient that the device is not working, by generating an audible signal for instance. If the power level is too low, the energy sensor feeds back to the transducer to increase the energy level, if possible, without exceeding a limit, illustratively 30 mW/cm².

In some embodiments, the transducer and the energy sensor are powered by built-in button batteries, many of which are commercially available from various manufacturers. The transducer, in one particular implementation, needs a current of 20 mA and a supply voltage of 1.5V. A 540 MAh battery, for example, can be expected to last 27 hours (540 mAh/20 mA) in this implementation, which exceeds a normal course of ultrasound stimulation of 20 minutes/day for four weeks. A device housing, batteries, or both could be customized depending on a desired overall size of an ultrasound device.

In one embodiment, LIPUS is used at 1.5 MHz with pulse repetition rate of 1.0 kHz, the pulse duty cycle is 20% (i.e., a 'pulse' duration of 200 μs and a 'null' duration for 800 μs), and the average intensity of the pulsed ultrasound is approximately 30 mW/cm². These characteristics may be exhibited, for example, using a piezoelectric transducer with a resistance of approximately 5Ω at 1.5 MHz frequency. Piezoelectric transducers of different characteristics can be accommodated after adjusting the signal amplitude to ensure desired ultrasound intensity, for example.

For one particular transducer having a contact area of approximately 2 cm², a pulsed ultrasound with an average power of 60 mW is used. Since the duty cycle in this example is 20%, the average signal power during the 'pulse' phase is 300 mW. This implies a root-mean-squared (RMS) voltage amplitude of approximately 3.87$V_{rms}$. However, a considerably higher voltage may be applied. A higher voltage might be used, for instance, to compensate losses incurred due to imperfect conversion efficiency from electrical to mechanical (ultrasound) energy and/or for imperfect ultrasound transmission from the transducer to tissues to be stimulated.

According to one embodiment, ultrasound energy is generated with an intensity of approximately 850 mW, corresponding to a square wave with peak amplitude 13$V_p$ during the 'pulse' period. A transducer unit having increased portability and relatively small size may be provided using a 3V battery, illustratively a Lithium Iodide battery such as used in pace makers, as a power source. To generate the above-noted $13V_p$ square wave, a larger supply voltage may be generated using a DC-DC converter.

Figure 5:
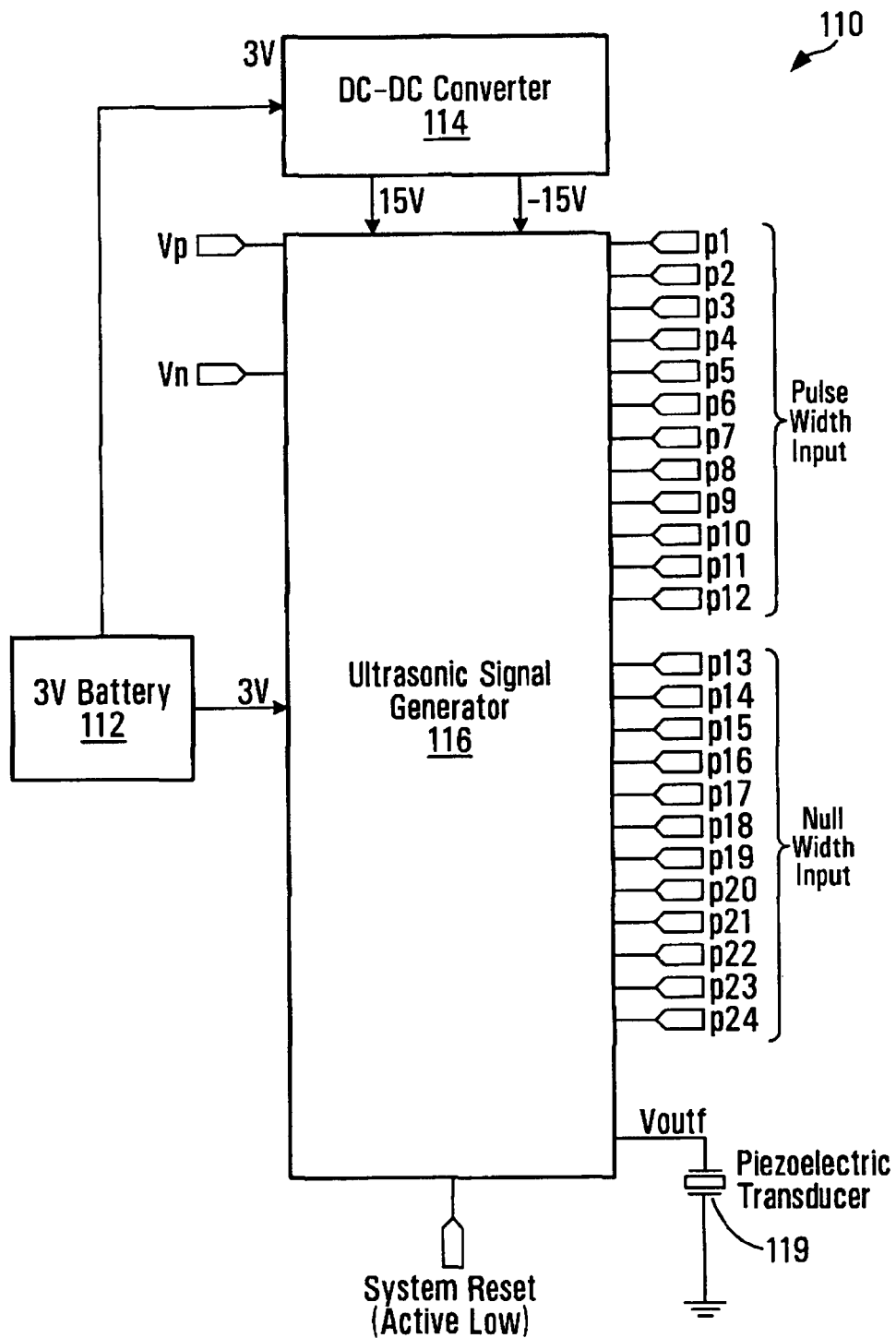
FIG. 5 is a block diagram of an ultrasound transducer unit according to a further embodiment of the invention.

FIG. 5 is a block diagram of one such ultrasound transducer unit according to a further embodiment of the invention. The example unit 110 includes a 3V battery 112 as a power source, a DC-DC converter 114 operatively coupled to the battery 112, an ultrasonic signal generator 116 operatively coupled to the battery, to the DC-DC converter and to a piezoelectric transducer 119.

Various forms of DC-DC converters suitable for use as the DC-DC converter 114 will be apparent to those skilled in the art. Those skilled in the art will also be familiar with piezoelectric transducers such as 119. It should be appreciated, however, that not all embodiments will necessarily employ a DC-DC converter, and that other types of ultrasound transducer than a piezoelectric transducer may be used. One example implementation of the ultrasonic signal generator 116 is shown in FIG. 7 and described below, although other designs may also be possible.

In the ultrasound transducer unit 110, the frequency of an ultrasonic signal generated by the piezoelectric transducer 119 can be adjusted by tuning voltages the $V_p$ and $V_n$ input to the ultrasonic signal generator 116. The input pins "Pulse width input" and "Null width input", represented in a binary format in FIG. 5 as p1 p2 p3 p4 p5 p6 p7 p8 p9 p10 p11 p12; and
p13 p14 p15 p16 p17 p18 p19 p20 p21 p22 p23 p24, are used to set the pulse repetition rate and duty cycle of resulting final waveform $V_{outf}$. In some embodiments, p1, p13 are the least significant bits (LSBs) in these inputs, and p12, p24 are the most significant bits (MSBs).

Figure 6:
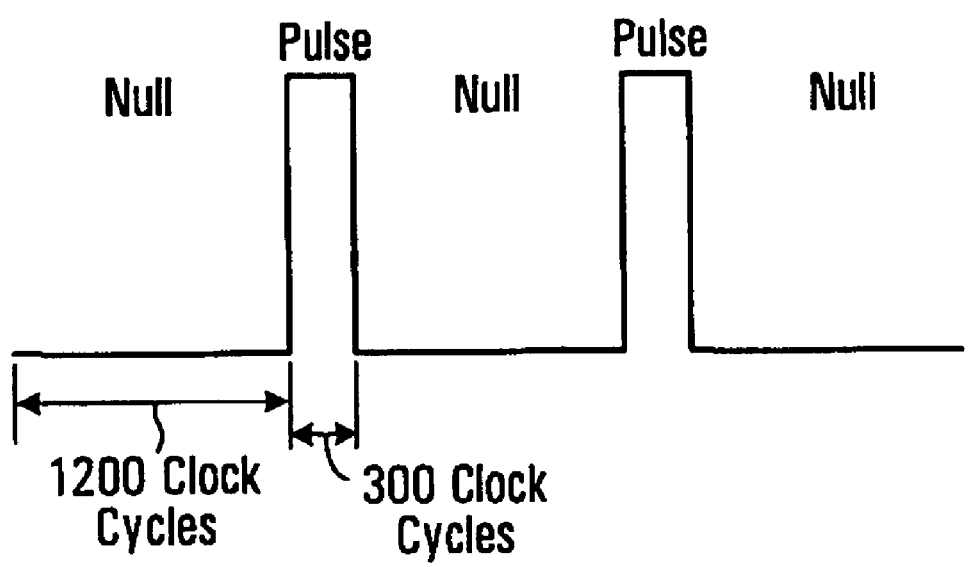
FIG. 6 is a plot showing example pulse characteristics for the ultrasound transducer unit of FIG. 5.

The "Null Width Input" may specify the length of a null period, as a number of clock cycles for instance, whereas "Pulse Width Input" sets a pulse duration, illustratively as a number of clock cycles during which the pulse is on. For example, setting "Null Width Input" to $010010110000_2$ ($=1200_{10}$) and "Pulse Width Input" to $000100101100_2$ ($=300_{10}$) produces the pulse characteristics shown in the plot of FIG. 6.

Figure 7:
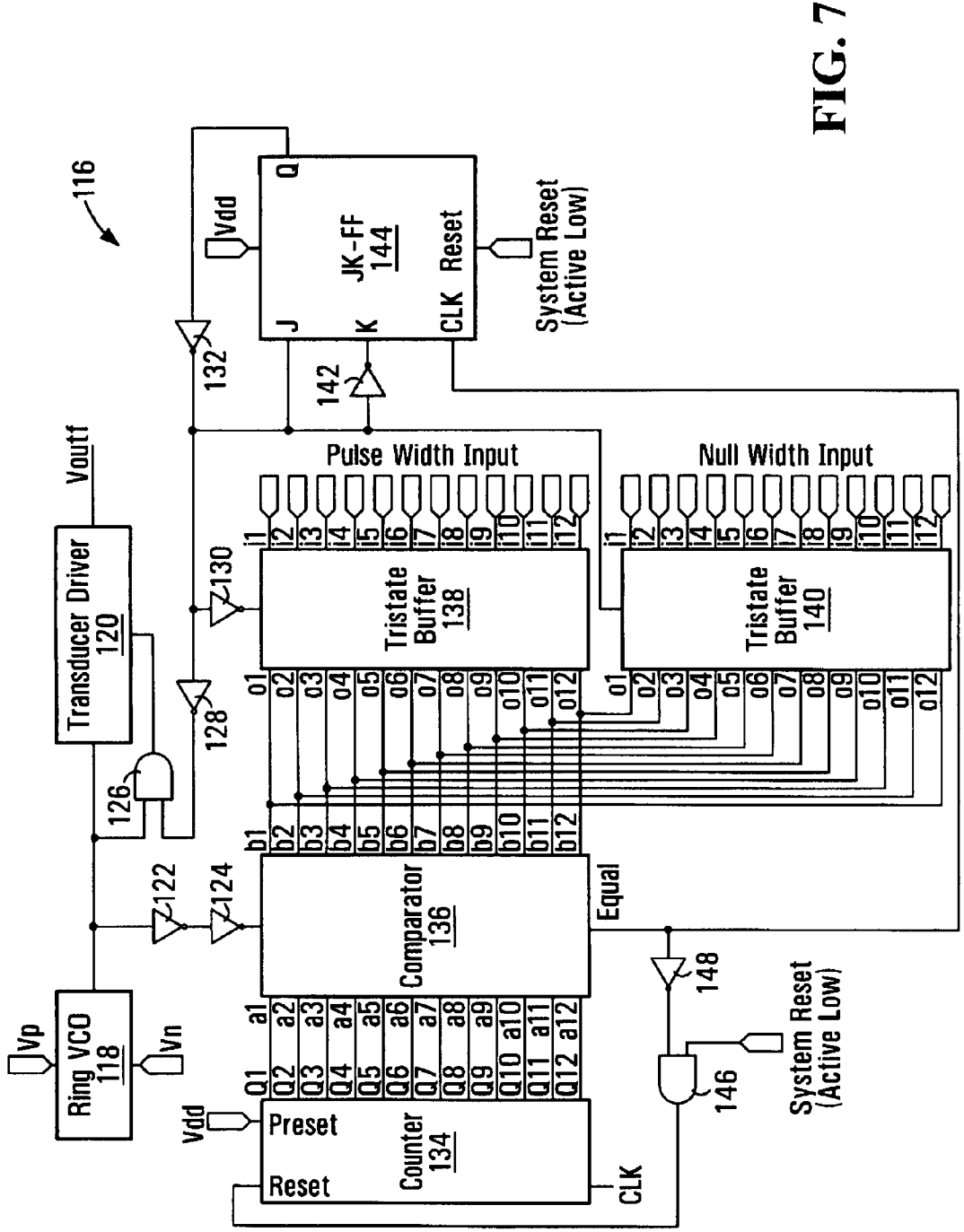
FIG. 7 is a block diagram of an example ultrasonic signal generator of the ultrasound transducer unit of FIG. 5.

FIG. 7 is a block diagram of an example ultrasonic signal generator of the ultrasound transducer unit of FIG. 5. The example generator 116 includes a ring VCO 118, a transducer driver 120, which is an amplifier, operatively coupled to the ring VCO, a counter 134, a comparator 136 operatively coupled to the ring VCO through two inverters 122, 124 and to the counter, two tristate buffers 138, 140 operatively coupled to the comparator, and a JK flip-flop 144 operatively coupled to the comparator, to the tristate buffers, and to the transducer driver. As shown, an output of the comparator 136 is operatively coupled to a reset input of the counter 134 through an inverter 148 and an AND gate 146 and to a clock (CLK) input of the JK flip-flop 144, and the Q output of the JK flip-flop is operatively coupled through an inverter 132 to its J input. The output of the inverter 132 is also operatively coupled to the K input of the JK flip-flop 144 through an inverter 142, to an enable input of the tristate buffer 140, to an enable input of the tristate buffer 138 through an inverter 130, and to the transducer driver 120 through another inverter 128 and an AND gate 126.

Various implementations of ring VCOs, amplifiers, counters, comparators, tristate buffers, JK flip-flops, inverters, and AND gates may be commercially available and/or may be apparent to those skilled in the art, and the present invention is not limited to any particular implementations of these components. Thus, the following functional description of these components will enable those skilled in the art to implement embodiments of the invention in any of multiple ways.

The ring VCO 118 is used to generate clock signals at 1.5 MHz for the entire ultrasonic signal generator 116. This same clock signal is fed to the transducer driver 120 to be amplified. The transducer driver 120 amplifies 3V digital signals to a higher voltage, illustratively 13V, ultrasound signal that drives the piezoelectric transducer 119 (FIG. 5). A pulsed signal programmed to 1.0 kHz, 20% duty cycle is used in one embodiment to modulate the ultrasound signals, thus producing desired pulsed ultrasound.

As discussed above, the "Pulse Width Input" and "Null Width Input" pins are used to program the 'pulse' width and 'null' width of a LIPUS signal. These inputs are fed into the ultrasonic signal generator 116 via the tristate buffers 138, 140. The two tristate buffers 138, 140 are alternately triggered into 'active' or 'high impedance' mode in a complementary fashion. During every clock cycle, only one of the tristate buffers 138, 140 is activated. The input state of the 'active' tristate buffer 138, 140 is transmitted to one set of input pins of the comparator 136 for comparison with the output of the counter 134.

The counter 134, on the other hand, keeps incrementing its count until its value matches that of the "Pulse Width Input" or "Null Width Input". At the moment when a match is detected, the comparator 136 asserts its 'Equal' pin 'high', which resets the counter 134 and toggles the JK Flip-flop 144. This brings about a change of phase from the 'null' to 'pulse' or vice versa. The ultrasonic signal generator 116 can be asynchronously reset by de-asserting the System Reset pin.

Illustrative examples of some of the components shown in FIG. 7 are described below, with reference to FIGS. 8 and 9.

Figure 8:
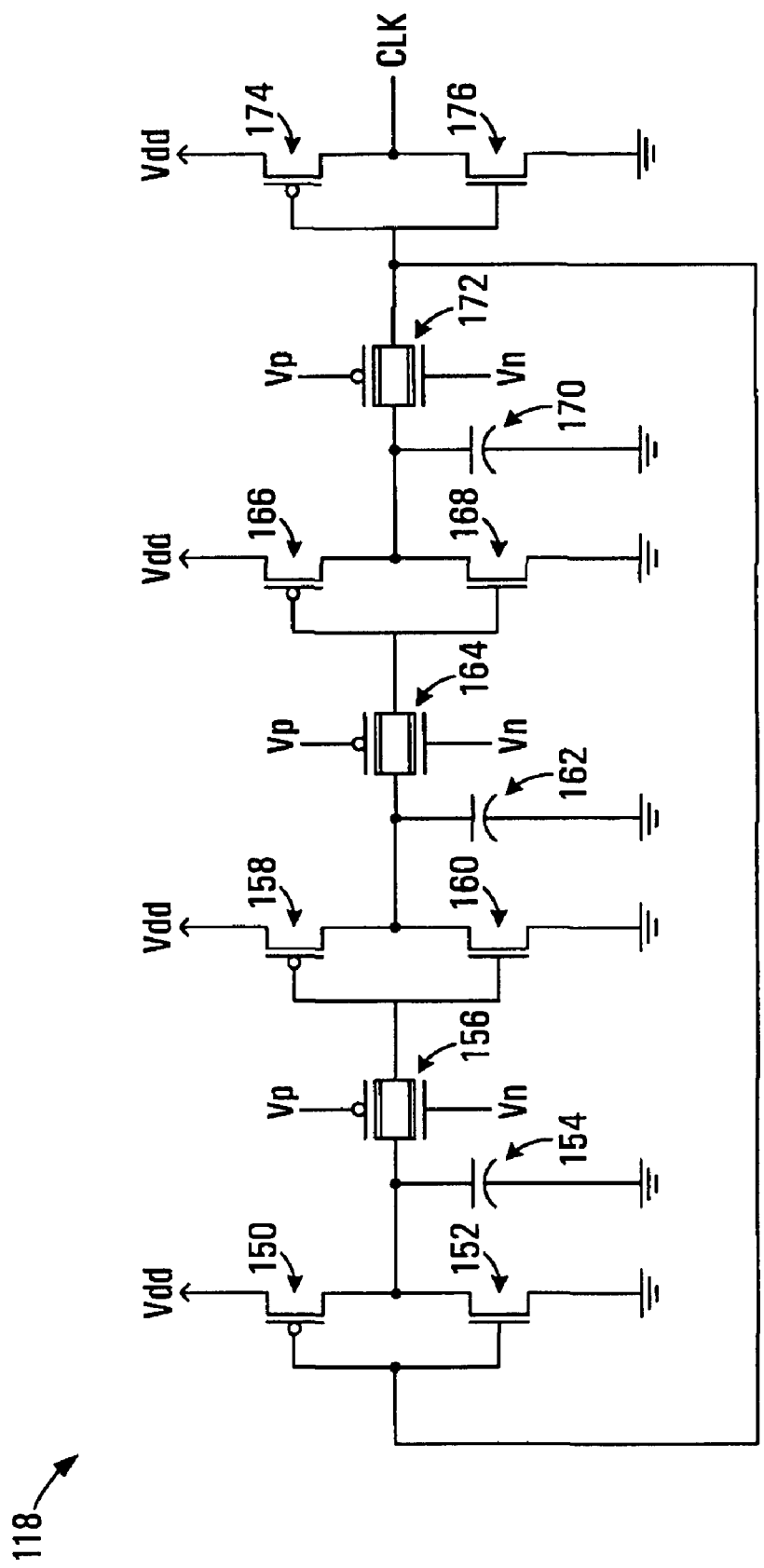
FIG. 8 is a schematic diagram of an example ring oscillator circuit that may be used as the ring Voltage Controlled Oscillator (VCO) of the ultrasonic signal generator of FIG. 7.

FIG. 8 is a schematic diagram of an example ring oscillator circuit that may be used as the ring VCO 118 of the ultrasonic signal generator of FIG. 7. The example ring VCO 118 includes transistors 150, 152, 158, 160, 166, 168, 174, 176 operatively coupled between $V_{dd}$ and ground, transmission gates 156, 164, 172 operatively coupled between transistor pairs and between $V_p$ and $V_n$, and capacitors 154, 162, 170 operatively coupled between the transistor pairs, transmission gates, and ground.

As noted above, the ring oscillator 116 provides the clock (CLK) signal for the ultrasonic signal generator 116 (FIG. 7). A ring oscillator may be preferred in some embodiments for its capability for generating relatively low frequency and for its tunability. In one embodiment, the capacitors 154, 162, 170 have values of C1=3.7 pF, and are used in each stage of the ring oscillator 116 to further reduce the oscillating frequency to that of a few MHz. In this example, the oscillation frequency of the CLK signal equals 1.5 MHz when $V_p$ and $V_n$ are set to 0.7V and 2.3V respectively.

Figure 9:
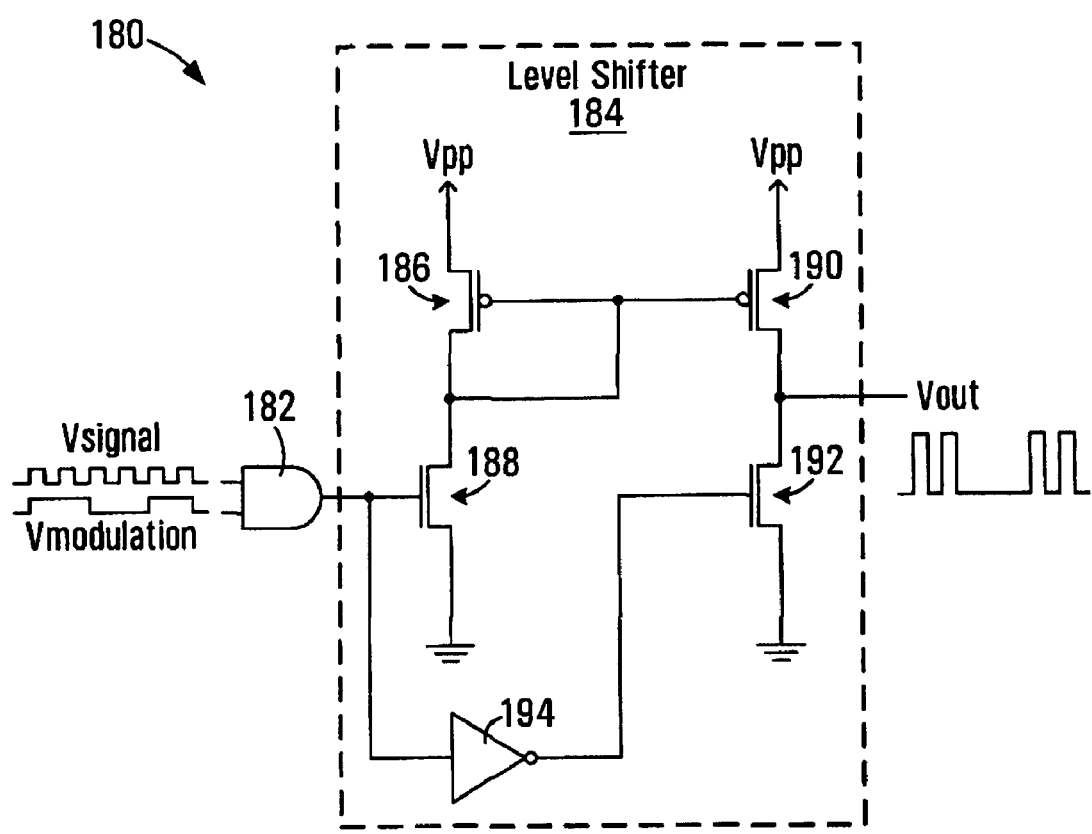
FIG. 9 is a schematic diagram of an example power amplifier circuit that may be used as the transducer driver of the ultrasound transducer unit of FIG. 7.

FIG. 9 is a schematic diagram of an example power amplifier circuit that may be used as the transducer driver 120 of the ultrasound transducer unit of FIG. 7. The example power amplifier 180 includes an AND gate 182 and a level shifter 184 operatively coupled to the AND gate. The level shifter 184 includes transistors 186, 188, 190, 192 operatively coupled between $V_{pp}$ and ground, with the control terminals, gate terminals in this example, of the transistors 188, 192 operatively coupled to the output of the AND gate 182. The gate terminal of the transistor 192 is operatively coupled to the output of the AND gate 182 through an inverter 194.

As noted above, the transducer driver 120 (FIG. 7) amplifies a voltage signal so as to drive a piezoelectric transducer. The first stage of the amplifier 180, which may be used as the transducer 120, includes the AND gate 182 acting as a modulator. The AND gate 182 modulates a 1.5 MHz digital signal with a 1.0 kHz, 20% duty-cycled pulsed signal in one embodiment. The remainder of the amplifier 186 is a level-shifter that amplifies a 3V pulsed signal to a higher peak level, such as 13V in an example described above.

High voltage (HV) n-channel Metal Oxide Semiconductor (NMOS) transistors and p-channel Metal Oxide Semiconductor (PMOS) transistors are used in the level-shifter 184 in the example shown. In one embodiment, these transistors 186, 188, 190, 192 are capable of withstanding high drain to source voltage $V_{DS}$. In the case of a resonant transducer resistance of 5Ω, a substantial driving current of magnitude up to 260 mA is expected. In order to satisfy this current driving capability, a number of transistors are used in parallel but for simplicity, each of these parallel combinations are represented by one transistor symbol in FIG. 9.

An implementation of the design shown in FIGS. 5 to 9 using 0.8 μm CMOS/DMOS High-Voltage process technology has been simulated. With an ultrasonic signal frequency of 1.49 MHz, pulse repetition frequency of 1.0 kHz, and pulse width of 200 μs, an output signal having 13V peak magnitude was observed. The average power consumption of the ultrasound transducer unit was 225 mW, out of which 170 mW will be delivered to the piezoelectric transducer 119.

What has been described is merely illustrative of the application of principles of embodiments of the invention. Other arrangements and methods can be implemented by those skilled in the art without departing from the scope of the present invention.

For example, a single device could incorporate multiple transducers and/or sensors. In a case where a patient has root resorption and/or root fracture from both outside and from inside for instance, then both a labial (outside) assembly and a lingual (inside) assemblies might contain respective LIPUS transducers, and possibly respective sensors, transmitters, and receivers.

In addition, devices according to further embodiments might also include other components than those specifically shown in the drawings and described above. Control parameters for an intra-oral device could be specified by a user through an interface other than a wireless transceiver for instance. Another variation would be to adapt the housing(s) for mounting to an intra-oral structure such as a bone or tissue other than a tooth.

Figure 10:
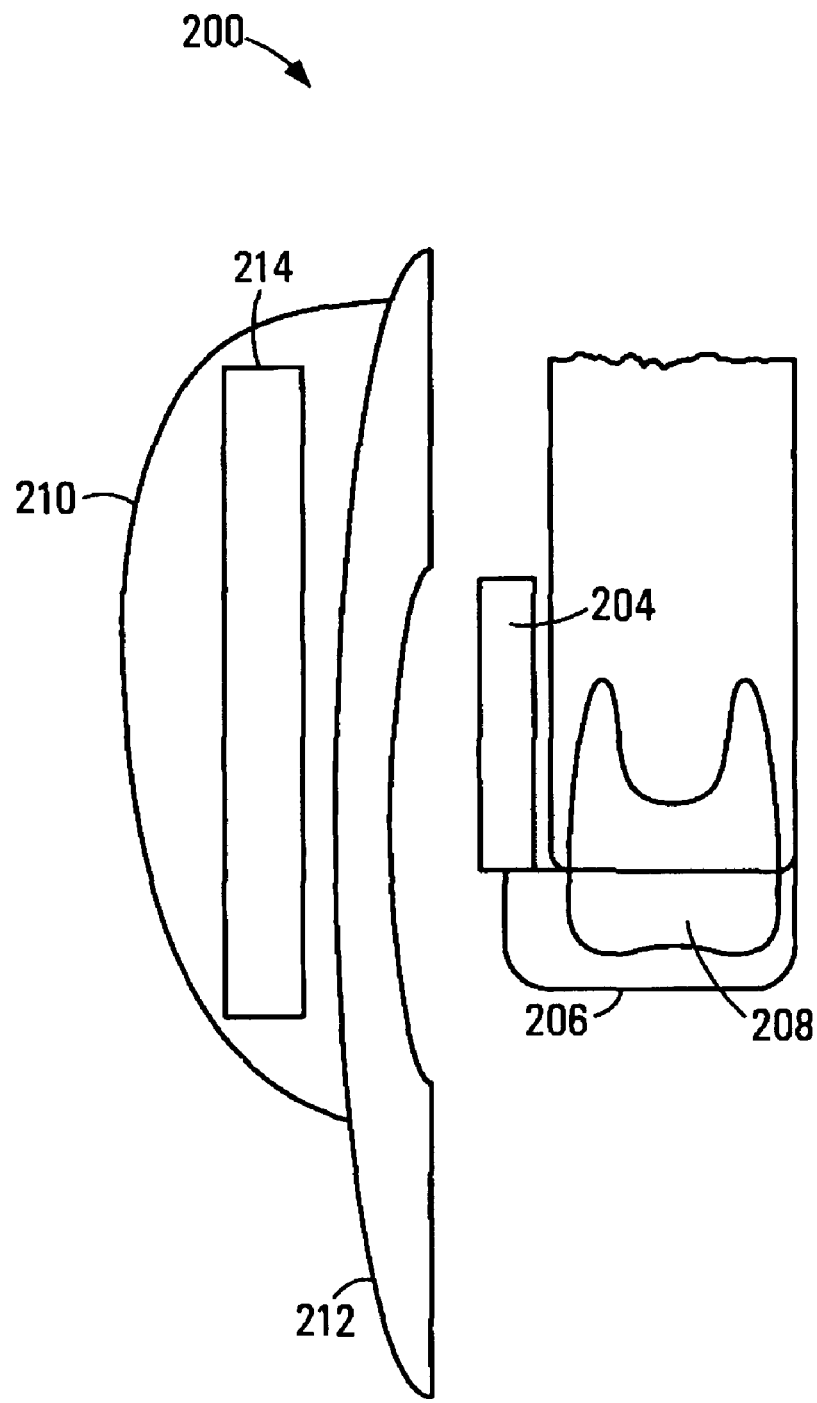
FIG. 10 is a front view illustrating the use of a device of another embodiment of the invention.

Regarding the mounting of housings, or more generally the positioning of a transducer and a sensor, further options are also contemplated. FIG. 10 is a front view illustrating the use of a device of another embodiment of the invention. In the arrangement shown in FIG. 10, a device 200 is used for stimulating growth of a jaw. The device 200 itself includes an ultrasound transducer, and possibly a UWB receiver, in a transducer housing 214 that is positioned proximate an application area of the jaw, such as just in front of the ear, using a positioning element. A rubber suction cup 210 is shown as an example of a suitable positioning element that may be used to removably mount the transducer housing 214 to the outside of a cheek 212 of a patient. Ultrasound gel may also be used to improve contact between the transducer housing 214 and the skin covering the jaw joint (in front of the ear). The transducer housing 214 might be further stabilized in place using a head apparatus (not shown) to apply pressure and hold the transducer housing 214 in place.

An ultrasound sensor unit including an ultrasound sensor and a UWB transmitter is also provided in the sensor housing 204 in the example shown. A sensor positioning element in the form of a crown 206 could be held on the upper last molar 208 in the side to be stimulated.

Figure 11:
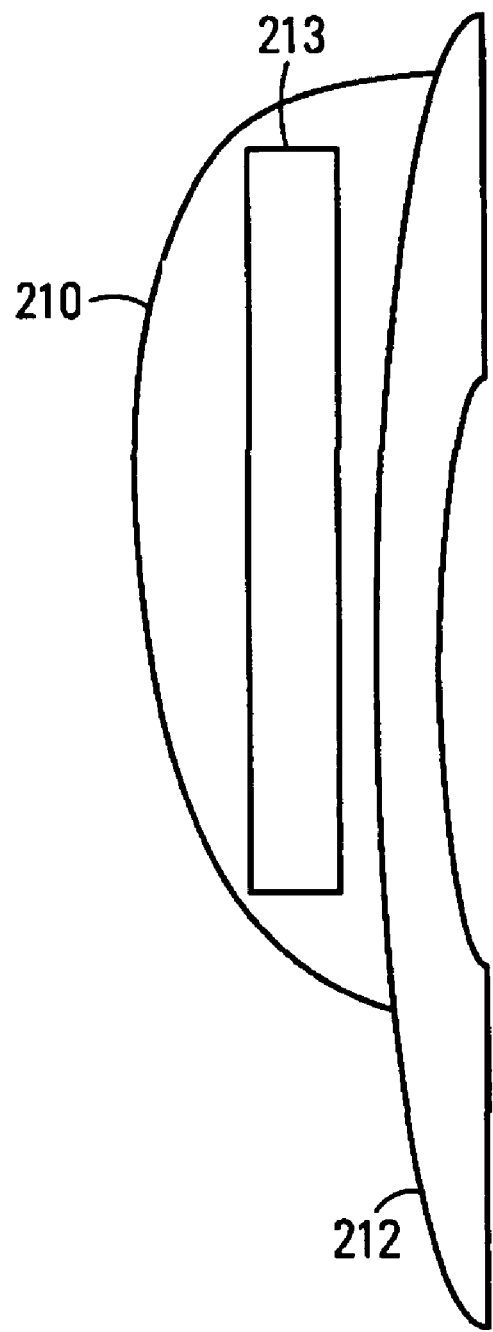
FIG. 11 is a front view illustrating the use of a device of yet another embodiment of the invention.

Variations of the device 200 may be or become apparent to those skilled in the art. Other positioning elements may be used instead of or in addition to the suction cup 210 and/or the crown 206, for instance. The positions of the transducer housing 214 and the sensor housing 204 could also be different than shown in FIG. 10, such as where the inside of the jaw is to be stimulated. In other embodiments, the transducer housing 214 or the sensor 204 could be mounted outside the cheek 212 instead of between the cheek and the jaw, as shown in FIG. 11. In this case, both a transducer and a sensor are enclosed in the same housing 213, which is positioned on the cheek 212 of a patient using the same positioning element, a suction cup 210 in the example shown. This example also illustrates the fact that the same housing and positioning element may be used for a transducer and a sensor, in which case feedback from the sensor to the transducer might not be provided through a UWB link or other wireless link.

Further variations are also possible.

Figure 12:
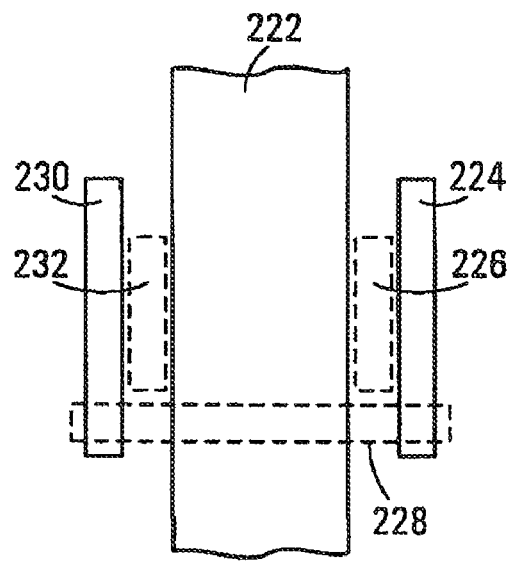
FIG. 12 is a side view illustrating the use of a device of a further embodiment of the invention.

FIG. 12 is a side view illustrating the use of a device of a further embodiment of the invention, and illustrates more generally the use of an ultrasound device to stimulate an application area and to sense ultrasound energy at a sensing area. A transducer housing 230 and a sensor housing 224, which respectively carry a transducer and receiver and a sensor and transmitter in some embodiments, may be positioned at portions of a body 222 of a patient. The respective positions of the transducer housing 230 and the sensor housing 224 are proximate an application area to which ultrasound energy is to be applied and a sensing area at which ultrasound energy is to be detected.

Such positioning of a transducer and a sensor may be accomplished using any of various forms of positioning elements. For stimulation of long bone growth, for example, a transducer/UWB receiver could be positioned on top of an epiphysial plate to be stimulated, while a sensor/UWB transmitter assembly is stabilized on the other side of the stimulated joint. The transducer housing 230 and the sensor housing 224 in this type of arrangement could be held in place using a temporary adhesive, hook and loop fastener on a garment, etc. This is shown generally in FIG. 12 at 226, 232. Another possible option would be to retain both housings 224, 230 on opposite sides of an application area using a belt or strap, as shown at 228.

Figure 13:
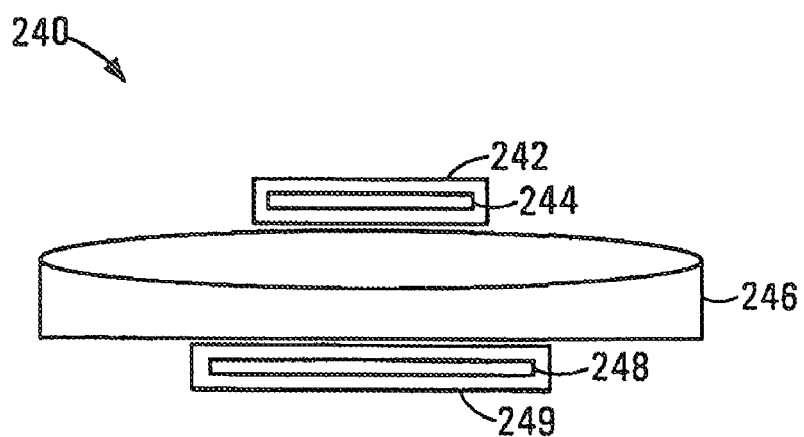
FIG. 13 is a side view illustrating the use of a device of another embodiment of the invention.

FIG. 13 is a side view illustrating the use of a device of another embodiment of the invention, which may be suitable for stimulating tissue or cells such as stem cells in a cell culture. The device 240 in this example includes two sealed units. A transducer unit 244 includes at least an ultrasound transducer, and possibly other components such as a controller and a wireless receiver. The transducer housing 242 seals the transducer unit 244. A sensor unit 248 similarly includes a sensor and a wireless transmitter, and is sealed inside the housing 249. Ultrasound stimulation can thereby be applied to a cell culture located between the ultrasound transducer unit 244 and the ultrasound sensor unit 248, in a cell or tissue culture dish 246 in the example shown. For example, the ultrasound transducer unit 244 might be floated in the culture medium of the cell culture.

In order to evaluate the stimulatory effect of LIPUS on cellular activity, freshly isolated rat bone marrow stem cells were experimented using a prototype LIPUS device. These cells were allowed to self-expand and after two weeks, cell counts and alkaline phosphatase measurements were performed. Comparisons between the cell counts of a control, an ultrasound treated group, and the original group illustrated that application of ultrasound stimulation increased stem cell expansion.

The application of ultrasound was also found to stimulate stem cell activity by increasing alkaline phosphatase expression. Three groups were used in the experiment: the original group before applying ultrasound, the control group that did not receive ultrasound application, and the ultrasound group that received ultrasound application for 20 minutes per day for 10 days.

Ultrasound transducers were securely attached under a flask containing the bone marrow stem cells. The experiment demonstrated that application of ultrasound is capable of stimulating cellular activity of bone marrow stem cells, in the form of increasing their replication (as indicated by the increased cell count) and increasing the alkaline phosphatase excretion.

To study the effect of ultrasound on cellular differentiation, the expression of Nucleostemin, a specific marker for bone marrow stem cells, was evaluated by Polymerase chain Reaction (PCR). It was seen that ultrasound stimulation up-regulated the expression of Nucleostemin when the bone marrow stem cells were cultured in a basic medium (Dulbecco's Modified Eagle Medium (DMEM), Hank's Balanced Salt Solution (HBSS; without phenol red), penicillin (10,000 U/mL solution), streptomycin (10,000 ug/mL solution), and heatinactivated fetal bovine serum (FBS)). When the bone marrow stem cells were induced to be differentiated into osteogenic lineage using osteogenic medium (supplemented with 100 nM dexamethasone, 10 mM glycerophosphate, and 0.05 mM ascorbic acid-2-phosphate), Nucleostemin was down-regulated. It was further down-regulated when ultrasound was applied. These results indicate that a LIPUS device can enhance stem cell differentiation into boneforming cell lineage.

It should thus be appreciated in view of the foregoing that embodiments of the invention need not necessarily be restricted to intra-oral devices. Ultrasound can be used to stimulate stem cell growth/expansion, for example. When culturing cells in vitro, an ultrasound transducer according to an embodiment of the invention, which is sterile, disposable, and emits controlled levels of ultrasound, could be provided in a culture flask for promotion of stem cell growth. Such a device may be implemented as a self-contained ultrasound stimulation device that includes an ultrasound transducer for generating ultrasound energy, and a housing sealing the ultrasound transducer.

Although described above primarily in the context of a device, the invention may be embodied in other forms, illustratively as a method of making such a device. In one embodiment, a method of making an ultrasound stimulation device involves providing a transducer housing for carrying an ultrasound transducer, providing a transducer positioning element operable to position the ultrasound transducer proximate an application area to which ultrasound energy is to be applied, and installing in the transducer housing an ultrasound transducer operable to generate ultrasound energy. Variations of such a method, including different ways of performing these operations, and further operations that may be performed in some embodiments, are also contemplated. Additional operations may include, for instance, installing other components in the transducer housing and/or in a different housing and interconnecting installed components.

Further variations of the specific examples disclosed herein are also possible. For example, an acoustic mirror could be provided in a transducer unit, on a transducer housing, or possibly as a separate element to reflect generated ultrasound toward an application area. An ultrasound mirror or reflector might be fabricated on a glass substrate with air micro-cavities inserted, for instance. Masks and photolithography (photoresist spinner, oven and mask exposure) could be used to define a pattern to be etched, using wet or dry etching, from the glass substrate. An ultrasonic transducer and such a reflector may then be bonded, using wafer bonding techniques for instance. A wafer bonding technique might be appropriate where the transducer is fabricated by depositing or sputtering electrodes (e.g., Al, Ag, Au or Ti) onto a high-efficiency piezoelectric material, such as PZT or copolyester.

The use of a high power-density piezoelectric transformer to drive a piezoelectric transducer is also contemplated.

An acoustic mirror and/or a piezoelectric transformer would decrease power usage and save battery life.

REFERENCES

[1] L. Andersson, "Dentoalveolar ankylosis and associated root resorption in replanted teeth. Experimental and clinical studies in monkeys and man". Swed Dent J Suppl, 1998;56: 175.

[2] M. Trope, "Luxation injuries and external root resorption etiology, treatment and prognosis". J Calif Dent Assoc, 2000;28: 8606.

[3] E. J. Barret and D. J. Kenny. "Avulsed permanent teeth: a review of the literature and treatment guidelines". Endod Dent Traumatol, 1997;13: 15363.

[4] S. Baumrind, E. Korn, and R. Boyd, "Apical root resorption in orthodontically treated adults". AJODO, 1996;110: 311-20.

[5] J. Mah, et. al, "Current status of root resorption". Biological Mechanics of Tooth Movement and Craniofacial Adaptation, Harvard Society for the Advancement of Orthodontics, 2000; 195-200.

[6] B. E. Machen, "Legal aspects of orthodontic practice: risk management concepts. Diagnosis, root resorption, and progress monitoring". AJODO, 1989;95:267-8.

[7] M. K. Caliskan and M. Turkun, "Prognosis of permanent teeth with internal resorption: a clinical review". Endod Dent Traumatol, 1997;13: 7581.

[8] J. P. Schatz, C. Hausherr, J. P. Joho, "A retrospective clinical and radiologic study of teeth reimplanted following traumatic avulsion". Endod Dent Traumatol, 1995;11: 2359.

[9] M. Trope, "Root resorption of dental and traumatic origin: classification based on etiology". Pract Periodontics Aesthet Dent, 1999;10: 51522.

[10] A. Majorana, E. Bardellini, G. Conti, E. Keller, S. Pasini, "Root resorption in dental trauma: 45 cases followed for 5 years". Dental Traumatology, 19 (5): 262-265, 2003.

[11] Iiker Alat, et. al., "The mechanical or electrical induction of medullary angiogenesis: will it improve sternal wound healing?". Medullary angiogenesis for sternal wound healing; vol. 31, no. 4, 2004.

[12] C. Saltzman, A. Lightfoot, and A. Amendola, "PEMF as Treatment for Delayed Healing of Foot and Ankle Arthrodesis". Foot & Ankle International; vol 25, No. 11 pp. 771-773, 2004.

[13] T. H. El-Bialy, T. J. Royston, R. L. Magin, C. A. Evans, A. M. Zaki, and L. A. Frizzell, "The effect of pulsed ultrasound on mandibular distraction". Ann. Biomed. Eng., 2002;30(10) :1251-61.

[14] T. H. El-Bilay, A. E. Zaki and C. A. Evans "Effect of ultrasound on rabbit mandibular incisor formation and eruption after mandibular osteodistraction". AJODO, 2003;124:427-34.

[15] T. El-Bialy, I. El-Shamy, T. M. Graber, "Repair of orthodontically induced root resorption by ultra-sound in humans". Am. J. Orthod. Dentofac. Orthop. 126(2): 186-93, August 2004.

[16] T. El-Bialy, et. al., "Treatment of Hemitacial Microsomia without Surgery: An Evidence-Based Approach". Proceeding of 6th International Congress, World Federation of Orthodontists, 8 Sep. 2005.

[17] Jie Chen, Tiejun Lv, Yingda Chen, and Jingyang Lv, "A Timing-jitter Robust UWB Modulation Scheme". Accepted in September 2005 to appear in IEEE Signal Processing Letter.

[18] Tiejun Lv, Jie Chen, and Yingda Chen, "High-order Monocycle Design and Orthogonal Code Division Multiplexing Time-hopping Multiple Access for UWB Communications". Submitted to IEEE Trans. on Communications.

[19] Yingda Chen, Jie Chen and Tie Lv, "A High Order Bi-phase Modulation Scheme for UWB Transmission". International Conference on Vehicular Technology 2004, Los Angeles, September 2004.

[20] A. Hajimiri and T. H. Lee, "A General Theory of Phase Noise in Electrical oscillators". IEEE Journal of Solid-state Circuits, Vol. 33, No. 2, pp. 179-194, February 1998.

[21] N. Retdian, S. Takagi, and N. Fujii, "Voltage Controlled Ring Oscillator with Wide Tuning Range and Fast Voltage Swing". IEEE Asia-Pacific Conference on ASIC, 2002.

[22] C. L. Tsai, W. H. Chang, and T. K. Liu, "Preliminary studies of duration and intensity of ultrasonic treatments on fracture Repair". Chin. J. Physiol. 35:21-26, 1992.

[23] D. A. Dalla-Bona, E. Tanaka, H. Oka, E. Yamano, N. Kawai, M. Miyauchi, T. Takata, K. Tanne, "Effects of ultrasound on cementoblast metabolism in vitro". Ultrasound Med Biol., June 2006;32(6):943-8.

We claim:

1. A device comprising:
   a miniaturized intra-oral ultrasound transducer operable to generate ultrasound energy;
   a miniaturized intra-oral biocompatible transducer housing for carrying the ultrasound transducer;
   a miniaturized intra-oral tooth-root transducer positioning element operable to position the ultrasound transducer adjacent and along a length of a tooth root and gum tissue to which the generated ultrasound energy is to be applied for ultrasound dental treatment;
   a miniaturized intra-oral ultrasound sensor operable to sense the ultrasound energy generated by the ultrasound transducer, and to provide a feedback signal to a miniaturized intra-oral controller disposed in the transducer housing and operatively coupled to the ultrasound transducer, the controller being operable to control an intensity of the ultrasound energy generated by the ultrasound transducer;
   a miniaturized intra-oral biocompatible sensor housing for carrying the ultrasound sensor; and
   a miniaturized intra-oral tooth-root sensor positioning element operable to position the ultrasound sensor adjacent and along a length of a tooth root and gum tissue, the tooth-root sensor positioning element operable to position the ultrasound sensor in a manner which separates the ultrasound sensor from the transducer with the tooth root and gum tissue to which the generated ultrasound energy is to be applied for ultrasound dental treatment;
   wherein the transducer positioning element comprises a releasable mounting portion for temporarily mounting the transducer housing to a support during the ultrasound dental treatment, and wherein the support comprises a tooth or other intra-oral structure and
   wherein the sensor positioning element comprises a releasable mounting portion for temporarily mounting the sensor housing to a support during the ultrasound dental treatment, and wherein the support comprises a tooth or other intra-oral structure.

2. The device of claim 1, wherein the transducer housing comprises:
   a transducer portion for carrying the ultrasound transducer; and
   a positioning portion comprising the transducer positioning element.

3. The device of claim 1, wherein the ultrasound transducer comprises a low intensity pulsed ultrasound (LIPUS) transducer.

4. The device of claim 1, further comprising:
   a battery disposed in the miniaturized intra-oral transducer housing and operatively coupled to the miniaturized intra-oral ultrasound transducer.

5. The device of claim 1, wherein the transducer positioning element comprises one of:
   an element for attachment to an orthodontic bracket that is fastened to the tooth or other intra-oral structure; and
   an element for attachment to the tooth or other intra-oral structure.

6. The device of claim 1, further comprising:
   a miniaturized intra-oral wireless transmitter operatively coupled to the ultrasound sensor; and
   a miniaturized intra-oral wireless receiver disposed in the transducer housing and operatively coupled to the controller,
   wherein the feedback signal is generated by the ultrasound sensor and is transmitted by the wireless transmitter and wherein the feedback signal is received by the controller through the wireless receiver.

7. The device of claim 6, wherein the wireless transmitter and the wireless receiver comprise an ultra-wideband (UWB) transmitter and a UWB receiver, respectively.

8. The device of claim 1, wherein the transducer positioning element comprises the sensor positioning element.

9. The device of claim 1, wherein the transducer positioning element and the sensor positioning element comprise a combination selected from a group consisting of:
   the transducer positioning element comprising an element for attachment to an orthodontic bracket that is fastened to a tooth or other intra-oral structure, and the sensor positioning element comprising a plate structured for retention by a portion of an oral cavity; and
   the transducer positioning element and the sensor positioning element comprising a tooth crown for attachment to the tooth.

* * * * *